US009753104B2

(12) United States Patent
Duffin et al.

(10) Patent No.: US 9,753,104 B2
(45) Date of Patent: Sep. 5, 2017

(54) SPECIMEN CONDITIONING AND IMAGING SYSTEM

(71) Applicant: TA INSTRUMENTS-WATERS L.L.C., Milford, MA (US)

(72) Inventors: Kyle P. Duffin, Shakopee, MN (US); Jason L. Chinavare, Minnetonka, MN (US); Thomas M. Hays, Blaine, MN (US); Troy D. Nickel, Minneapolis, MN (US); Chrysanthi Williams, Minnetonka, MN (US); Anthony Blythe, Calgary (CA); Jeffrey Frank Dunn, Calgary (CA); Steven Michael Jones, Calgary (CA); Janet Lenore Ronsky, Calgary (CA)

(73) Assignee: TA Instruments-Waters L.L.C., Milford, MA (US)

( * ) Notice: Subject to any disclaimer, the term of this patent is extended or adjusted under 35 U.S.C. 154(b) by 469 days.

(21) Appl. No.: 14/466,163

(22) Filed: Aug. 22, 2014

(65) Prior Publication Data
US 2016/0054403 A1 Feb. 25, 2016

(51) Int. Cl.
G01R 33/30 (2006.01)
G01N 1/38 (2006.01)
G01N 33/483 (2006.01)

(52) U.S. Cl.
CPC ............. G01R 33/307 (2013.01); G01N 1/38 (2013.01); G01N 33/4833 (2013.01); G01N 2203/0089 (2013.01); G01N 2223/307 (2013.01)

(58) Field of Classification Search
CPC .... G01R 33/307; G01N 1/38; G01N 33/4833; G01N 2203/0089; G01N 2223/307
See application file for complete search history.

(56) References Cited

U.S. PATENT DOCUMENTS

| 6,992,486 | B2 | 1/2006 | Srinivasan |
| 7,268,552 | B1* | 9/2007 | Gerald, II ............. G01N 24/08 324/303 |
| 7,694,593 | B2 | 4/2010 | Owens et al. |
| 7,846,715 | B2 | 12/2010 | Owens et al. |
| 9,051,541 | B2 | 6/2015 | Othman et al. |
| 2006/0245933 | A1 | 11/2006 | Balch et al. |
| 2008/0069737 | A1* | 3/2008 | Fasulka ................. B01L 3/5025 422/400 |

(Continued)

OTHER PUBLICATIONS

Donoghu et al., "Use of Magnetic Resonance Imaging to Analyze the Performance of Hollow-Fiber Bioreactors", Worcester Polytechnic Institute, pp. 285-300 (1992).

(Continued)

*Primary Examiner* — Rodney Bonnette
(74) *Attorney, Agent, or Firm* — McCarter & English, LLP; Deborah M. Vernon; Heath T. Misley

(57) ABSTRACT

A conditioning system includes a sample chamber capable of receiving a specimen as well as first and second specimen-holding fixtures positioned within the sample chamber and configured to apply mechanical stimulation to a specimen held by the fixtures. The system has at least one port capable of providing a fluid to the sample chamber. The chamber is sized and shaped so that it can be inserted into an imaging device which can record images of a specimen held by the fixtures.

26 Claims, 5 Drawing Sheets

(56) References Cited

U.S. PATENT DOCUMENTS

2012/0062226 A1* 3/2012 Pielak .................. G01R 33/307
                                                          324/309

OTHER PUBLICATIONS

Heath et al., "Magnetic Resonance Imaging and Modeling of Flow in Hollow-Fiber Bioreactors", AIChE Journal, vol. 36, No. 4, pp. 547-558 (Apr. 1990).

Lohezic et al., "Optimized Radiofrequency Coil Setup for MR Examination of Living Isolated Rat Hearts in a Horizontal 9.4T Magnet", Magnetic Resonance in Medicine, pp. 1-8 (2014).

Richardson et al., "A Viable Isolated Tissue System: A Tool for Detailed MR Measurements and Controlled Perturbation in Physiologically Stable Tissue", Magnetic Resonance in Medicine, 69, pp. 1603-1610 (2013).

International Search Report and Written Opinion for PCT/US2015/046259 mailed Nov. 12, 2015 p. 1-15.

* cited by examiner

SPECIMEN CONDITIONING AND IMAGING SYSTEM

BACKGROUND

This disclosure relates to a sample chamber for containing a biomaterial.

In FIG. 1 of U.S. Pat. No. 7,846,715 (the '715 patent) a sample chamber 100 is disclosed which allows various types of tissues and other types of biomaterials to be conditioned. The contents of the '715 patent are incorporated herein by reference. To allow for the introduction of fluids (or other content) into the sample chamber 100, the chamber is sealed to define a chamber volume 102 within which a specimen 104 is positioned. The sample chamber 100 includes two push rods 106, 108 that allow the specimen 104 to be held along a vertical axis. The orientation and position of the push rods 106, 108 may be manually changed for adjusting the specimen 104. One or both of the rods 106, 108 can be moved (e.g. up and down or rotated) by a motor to provide mechanical stimulation to the specimen 104. A user-defined conditioning profile specifies a desired mechanical stimulation of a specimen 104.

The sample chamber 100 also includes a transparent chamber window 114 that allows the chamber volume 102 and the specimen 104 to be viewed during conditioning. Various types of transparent material (e.g., plastics, glass, etc.) may be used to produce the window 114 while still providing the appropriate structural integrity needed for conditioning the specimen 104 with the sample chamber 100. The window 114 is secured against a compliant element (e.g. an O-ring) with six fasteners in order to provide a leak-proof seal between the chamber 100 and the window 114. These fasteners (e.g. screws) apply compression around the perimeter of the sealing area. If there isn't enough compression all along the element, the seal will leak. The number and placement of the fasteners is determined by the pressure and stiffness of the elements involved.

Sometimes it may be desireable to obtain one or more images of the specimen 104 after the specimen has been placed in the chamber 100 (e.g. part way through a mechanical stimulation conditioning profile). These images can be obtained via a magnetic resonance imaging (MRI) device. Currently, in order to capture these images, the chamber 100 must be opened up by removing the window 114. The specimen 104 is then removed from the chamber and placed in a container which has a geometry and is made of materials that make the container compatible for use in an MRI device. The container is then placed in an MRI device and images of the specimen 104 are captured. The specimen 104 often contains living cells that are very sensitive to environmental changes (e.g. exposure to air flow can kill them). The temperature is also critical. If the cells experience significant temperature changes they will die. This temperature window is relatively small (e.g. around 2° C.). Having to transfer the specimen 104 from the chamber 100 to the MRI container in order to capture an image of the specimen increases the risk of damaging or killing the specimen. Again, exposing the cells to an environment external to a container in which the cells are contained may weaken or kill the cells.

SUMMARY

All examples and features mentioned below can be combined in any technically possible way.

In one aspect, a conditioning system includes a sample chamber capable of receiving a specimen as well as first and second specimen-holding fixtures positioned within the sample chamber and configured to apply mechanical stimulation to a specimen held by the fixtures. The system has at least one port capable of providing a fluid to the sample chamber. The chamber is sized and shaped so that it can be inserted into an imaging device which can record images of a specimen held by the fixtures.

Embodiments may include one of the following features, or any combination thereof. The imaging device is a magnetic resonance imaging device. The chamber is substantially in the shape of a cylinder. An outside diameter of the cylindrical chamber is sized so that the chamber can be received into a bore in the imaging device. The conditioning system includes one or more of plastic, thermoplastic, polyether ether ketone, polyvinylidene fluoride, polypropylene, silicone and polycarbonate. The first and second specimen-holding fixtures include polyether ether ketone. The sample chamber includes at least one substantially transparent window that includes one or more of polyvinylidene fluoride and polycarbonate. Fluid flow through the chamber can be maintained while the chamber is in the imaging device. The specimen can be mechanically stimulated while the chamber is in the imaging device. The imaging device is selected from the group of imaging devices that do medical imaging, medical scanning, X-ray radiography, medical ultrasonography, ultrasound, endoscopy, elastography, tactile imaging, thermography, medical photography, clinical imaging, clinical scanning, diagnostic imaging, radiological scanning, radiological imaging, nuclear medicine functional imaging, positron emission tomography and computed tomography. The conditioning system includes one or more materials (i) having a dielectric strength of at least about 7800 volts/mm, and (ii) which allow substantially artifact free images of the specimen to be recorded. The conditioning system includes one or more materials (i) having a dielectric constant of between about 2.2 to about 8.4, and (ii) which allow substantially artifact free images of the specimen to be recorded.

In another aspect, a conditioning system includes a sample chamber capable of receiving a specimen as well as first and second specimen-holding fixtures positioned within the sample chamber and configured to apply mechanical stimulation to a specimen held by the fixtures. There is at least one port capable of providing a fluid to one or more of the sample and the sample chamber, the conditioning system being made of materials which allow a specimen contained in the chamber to be imaged by an imaging device into which the chamber has been inserted.

Embodiments may include one of the above and/or below features, or any combination thereof.

In another aspect, a method of conditioning and imaging a specimen includes providing a sample chamber capable of receiving the specimen, and placing the specimen into the chamber such that the specimen is located between first and a second specimen-holding fixtures positioned within the sample chamber. The fixtures are adjusted so that the fixtures hold the specimen. Mechanical stimulation is applied to the specimen held by the fixtures by moving at least one of the fixtures. The chamber is inserted into an imaging device. An image of the specimen is recorded.

Embodiments may include one of the above and/or below features, or any combination thereof. The chamber includes polypropylene.

DETAILED DESCRIPTION

The description below describes a conditioning system that can provide physical stimulation to a specimen (e.g. of living cells) and allow the specimen to be imaged. The system includes a sample chamber capable of receiving the specimen as well as first and second specimen-holding fixtures positioned within the sample chamber and configured to apply mechanical stimulation to the specimen held by the fixtures. The chamber is sized and shaped so that it can be inserted into an imaging device which can record images of the specimen held by the fixtures. The chamber can also be made of materials which (a) enable the imaging device to accurately record images of the specimen, and (b) can be sterilized in an autoclave chamber.

Figure 1:
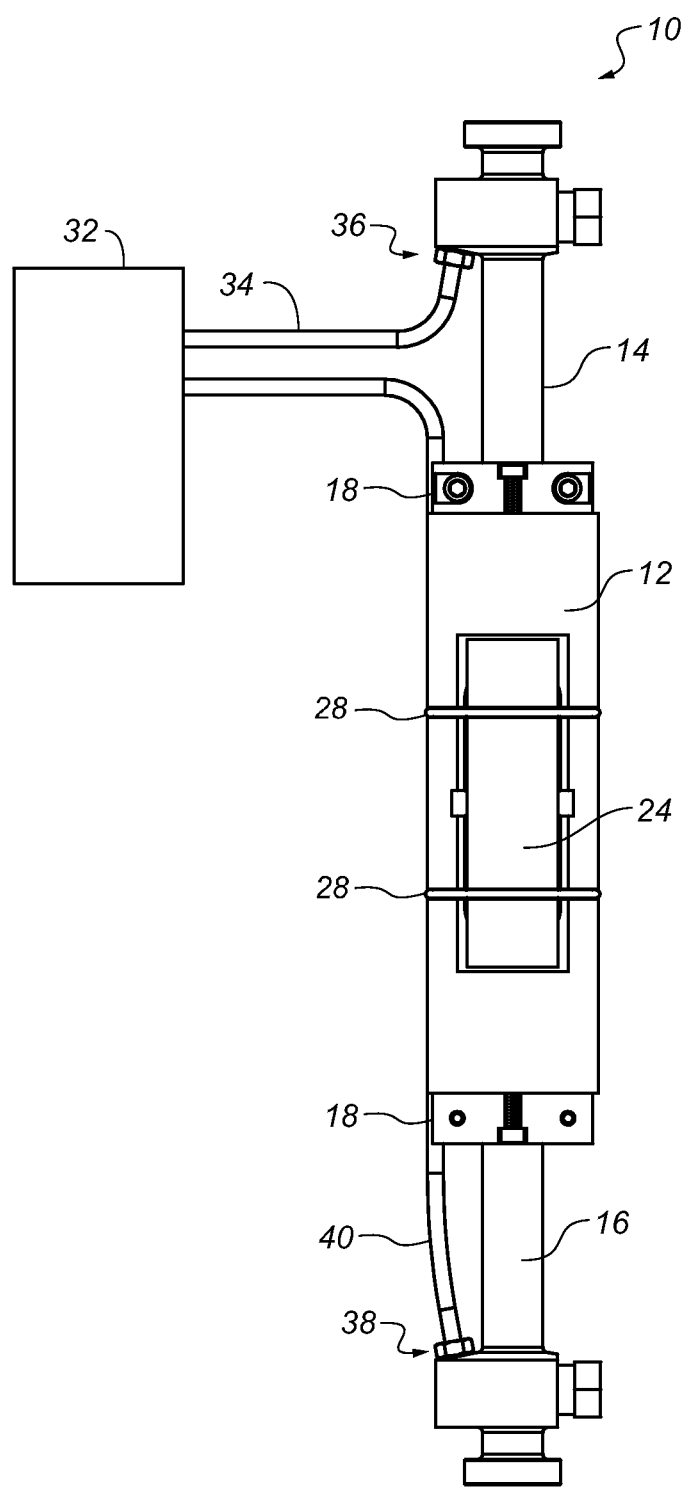
FIG. 1 is side view of a sample chamber.
Figure 2:
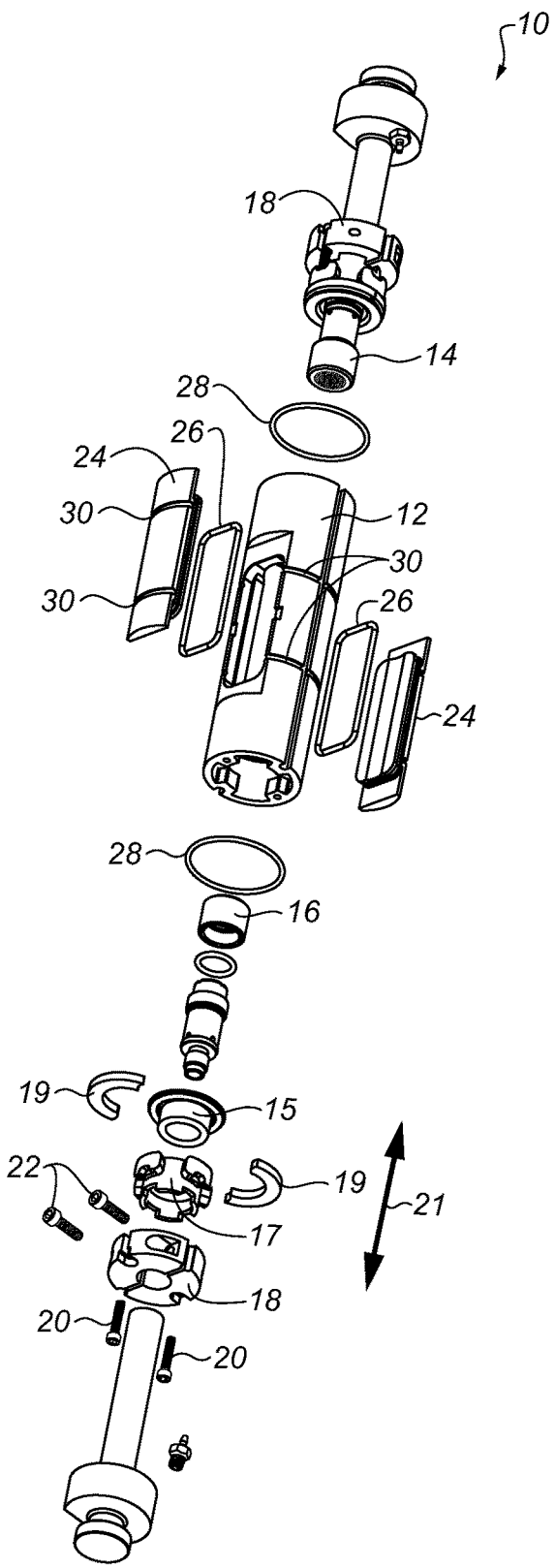
FIG. 2 is an exploded view of the chamber of FIG. 1.

With reference to FIGS. 1 and 2, a portion 10 of a conditioning system includes a sample chamber 12 that is capable of receiving a specimen (not shown). The chamber 12 is sized and shaped so that it can be inserted into an imaging device (not shown) which can record images of the specimen (e.g. that may include living cells) held by fixtures within the chamber. The chamber 12 in this example is generally in the shape of a cylinder. An outside diameter of the cylindrical chamber 12 is sized so that the chamber can be received into the bore of an imaging device (e.g. a magnetic resonance imaging (MRI) device). In this example, the outside diameter of the chamber 12 is preferably about 35 mm.

Any parts of the system that could interfere with accurate images of the specimen being recorded should preferably be made of materials which allow substantially artifact free images of the specimen to be recorded by an imaging device into which the chamber has been inserted. Generally speaking, these parts should be made of a plastic or thermoplastic. The parts are preferably made of materials having a dielectric strength of at least about 7800 volts/mm, and/or a dielectric constant of between about 2.2 to about 8.4. The chamber 12 is preferably made of a material that includes polypropylene or a similar material. This type of material will not interfere with an MRI device recording images of a specimen inside the chamber. This type of material is preferably made of a material that can withstand sterilization in an autoclave chamber.

First and second specimen-holding fixtures 14 and 16 are positioned within the chamber 12 and are configured to apply mechanical stimulation to a specimen held by the fixtures (described in further detail below). The first and second fixtures 14 and 16 each are made of a material that includes polyether ether ketone (30% glass filled) which will not interfere with MRI imaging. A pair of split fixture locks 18 are each loosely secured to respective ends of the chamber 12 by a pair of screws 20. A pair of screws 22 can be tightened to secure each fixture within a respective fixture lock. The screws are loosened shortly before the fixtures 14 and 16 are moved to apply mechanical stimulation to a specimen within the chamber 12. The fixture locks 18 are preferably made of a material that includes polypropylene. The screws 20 and 22 are preferably made of a material that includes polypropylene and/or polyvinylidene fluoride which will not interfere with MRI imaging.

A pair of substantially transparent windows 24 are provided on the chamber 12 to allow a person to view a specimen within the chamber. The windows 24 are preferably made of a material that includes polycarbonate and/or polyvinylidene fluoride which will not interfere with MRI imaging. A pair of sealing silicone O-rings 26 provide a respective fluid proof seal for each of the windows 24. The windows 24 and O-rings 26 are secured to the chamber 12 by a pair of securing silicone O-rings 28 which reside in grooves 30 on the chamber and windows. Silicone will not interfere with MRI imaging. Each of the specimen holding fixtures 14 and 16 is connected to the chamber 12 by a silicone diaphragm 15. An outer disc region of the silicone diaphragm 15 is secured to the chamber 12 by a rotatable locking retainer 17 and rotatable retainer seal disc halves 19 which lock and seat within each end of the chamber 12. An inner disc region of the silicone diaphragm 15 interfaces with the specimen holding fixture 16. The silicone diaphragm 15 provides a fluid proof seal that enables displacement and force transfer via the fixture 16 with minimal signal error. Each silicone diaphragm permits one of the specimen holding fixtures 14 and 16 to displace and rotate along an axis 21 relative to the chamber 12.

Referring to FIG. 1, a fluid pump unit 32 pumps fluid from a fluid reservoir within the pump unit into an inlet conduit 34 which is preferably flexible. This flexibility allows the pump unit 32 and fixture 14 to be moved relative to each other. This fluid (e.g. a saline solution or cell culture media) can contain nutrients and be provided at a temperature to support the health and growth of living cells in the specimen inside the chamber 12. From the conduit 34 the fluid passes through a port 36 in the fixture 14 and travels through an axial bore in this fixture. The fluid can then enter the chamber 12 and/or be perfused through the specimen. The fluid exits the chamber 12 via an axial bore in the fixture 16 and passes out of this fixture via a port 38. The fluid then passes through a flexible outlet conduit 40 and renters the fluid pump unit 32. This flexibility allows the pump unit 32 and chamber 12 to be moved relative to each other. A portion of the conduit 40 is supported in an external channel in the chamber 12. The fluid can be returned to the fluid reservoir inside the pump unit 32 or get passed to a separate waste fluid container within the pump unit.

The pump unit 32 can include a filter which filters the fluid prior to the fluid exiting the pump unit. The pump unit 32 can also include a filter which filters the fluid when the fluid is returned to the pump unit prior to the fluid entering the fluid reservoir. If the pump unit uses an electric motor to pump the fluid, electrical power can be supplied to the motor via a battery within the pump unit or from AC mains through an extension cord. It is preferable that the pump unit is portable so that it can be moved with the chamber 12 as the chamber is moved.

Referring to FIG. 2, the procedure for loading a specimen into the chamber 12 is as follows. The portion 10 of the conditioning system is disassembled, cleaned and sterilized. The portion 10 is then reassembled except for one of the windows 24. Next, a specimen is placed into the chamber 12 through an opening in the chamber that will be covered by the window 24. The fixtures 14 and 16 are adjusted (i.e. moved) along their long axes so that the specimen is located between and held by the fixtures. The screws 22 for each fixture are then tightened to lock the fixture in place. The chamber 12 is then filled up with fluid and the window 24 is placed onto the chamber over its respective O-ring 26. The O-rings 28 are then rolled into the respective grooves 30 to hold the two windows 24 in place on the chamber. In place of or in addition to the O-rings 28, two overlapping wraps of tape (e.g. Kapton tape) are circumferentially applied to each end of the windows 24 and the chamber 12 to secure the windows to the chamber. If the O-rings 28 are not used then the grooves 30 are not provided on the chamber 12 and the windows 24.

Figure 3:
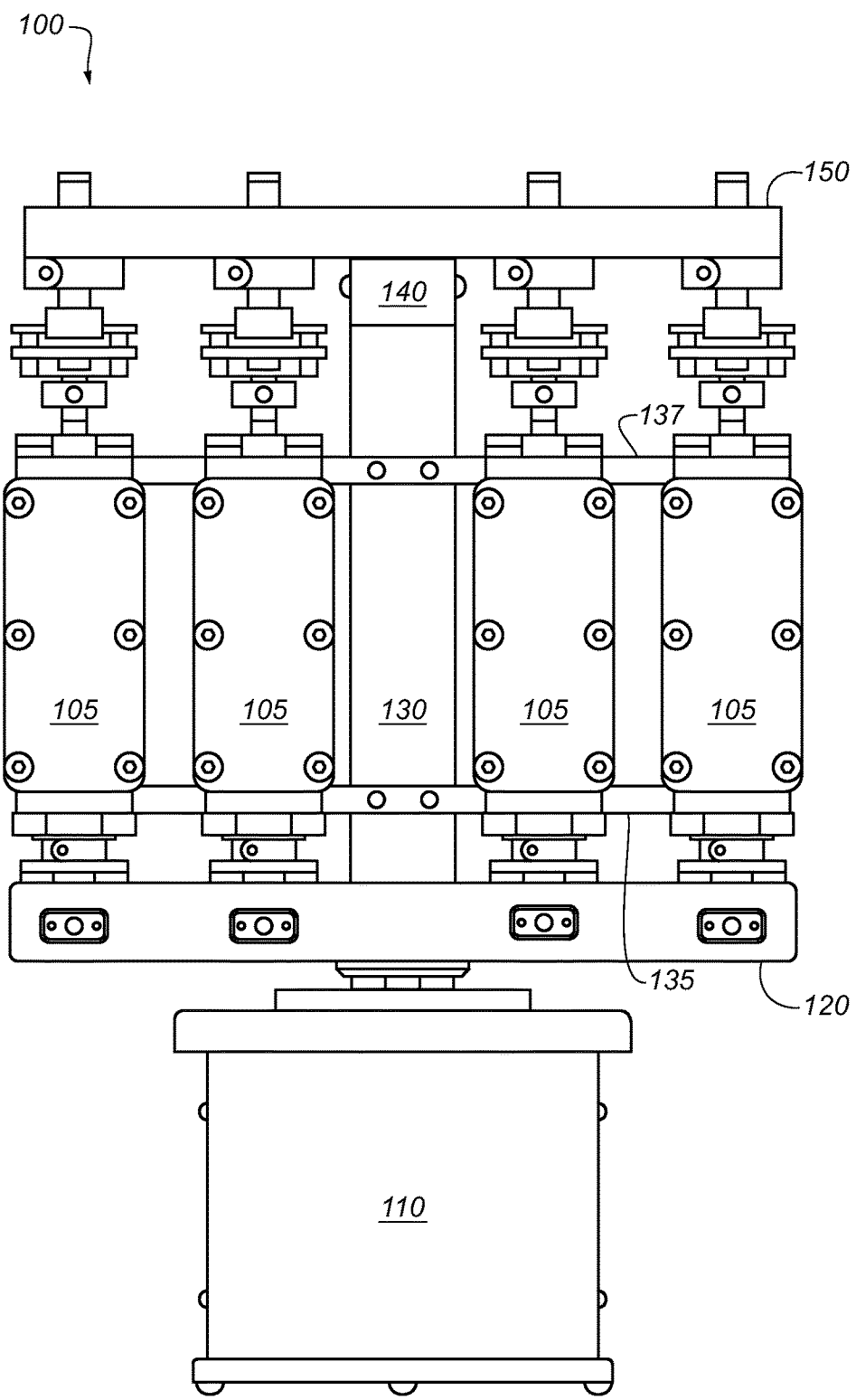
FIG. 3 is a front view of a conditioning frame of a multi-sample conditioning system.

FIG. 3 illustrates a front view of a conditioning frame 100 of a multi-sample conditioning system. Various types of conditioning systems are available from the ElectroForce Systems Group of Bose Corporation. This conditioning system is disclosed in U.S. Pat. No. 7,694,593 which is incorporated herein by reference. The conditioning frame 100 includes a power-head assembly 110, push-bar assembly 120, a load-frame beam 130, a reaction bracket 140, and a reaction crossbar 150. The power-head assembly 110 is rigidly attached to the load-frame beam 130. The load-frame beam 130 is attached to the reaction bracket 140. The reaction bracket 140 supports the crossbar 150. The load-frame beam 130 supports a lower chamber mounting bar 135 and an upper chamber mounting bar 137. In the example shown in FIG. 1-3, the upper and lower mounting bars support four sample chambers 105 but is not limited to four sample chambers.

The power-head assembly 110 includes a rigid housing attached to the load-frame beam 130 and an actuator (not shown) mounted to the rigid housing. The actuator drives the push-bar assembly 120. Although FIG. 1 shows a linear arrangement of sample chambers, other configurations of sample chambers may also be used. For example, the sample chambers may be arranged in a radial or circumferential pattern. In other configurations, a sample chamber may support multiple samples. In other configurations, any number of sample chambers may be used to hold the multiple samples.

The actuator is preferably a linear motor and more preferably a moving magnet linear motor although other actuators may be used in other embodiments. An example of a moving magnet linear motor is disclosed in U.S. Pat. No. 6,405,599 issued on Jun. 18, 2002 herein incorporated by reference in its entirety. Examples of other types of actuators that may be used include but are not limited to a voice coil, a linear servomotor, a rotary motor with a drive mechanism, a hydraulic actuator, a pneumatic actuator, and a piezoelectric actuator. The push-bar assembly 120 couples an axial displacement of the push-bar assembly 120 to a sample grip inside the sample chamber 105.

The sample chambers 105 can be replaced by one or more chambers 12 shown in FIGS. 1 and 2. The arrangement for mounting chambers in the conditioning frame 100 would need to be modified to accept the chamber 12. Once the chamber 12 is mounted in the conditioning frame 12, the screws 22 for each fixture 14 and 16 are loosened. The conditioning system is then operated to move the fixtures to apply a mechanical stimulation cycle to the specimen held by the fixtures within the chamber 12. After the mechanical stimulation cycle is finished, the chamber 12 is removed from the frame 100.

Figure 4:
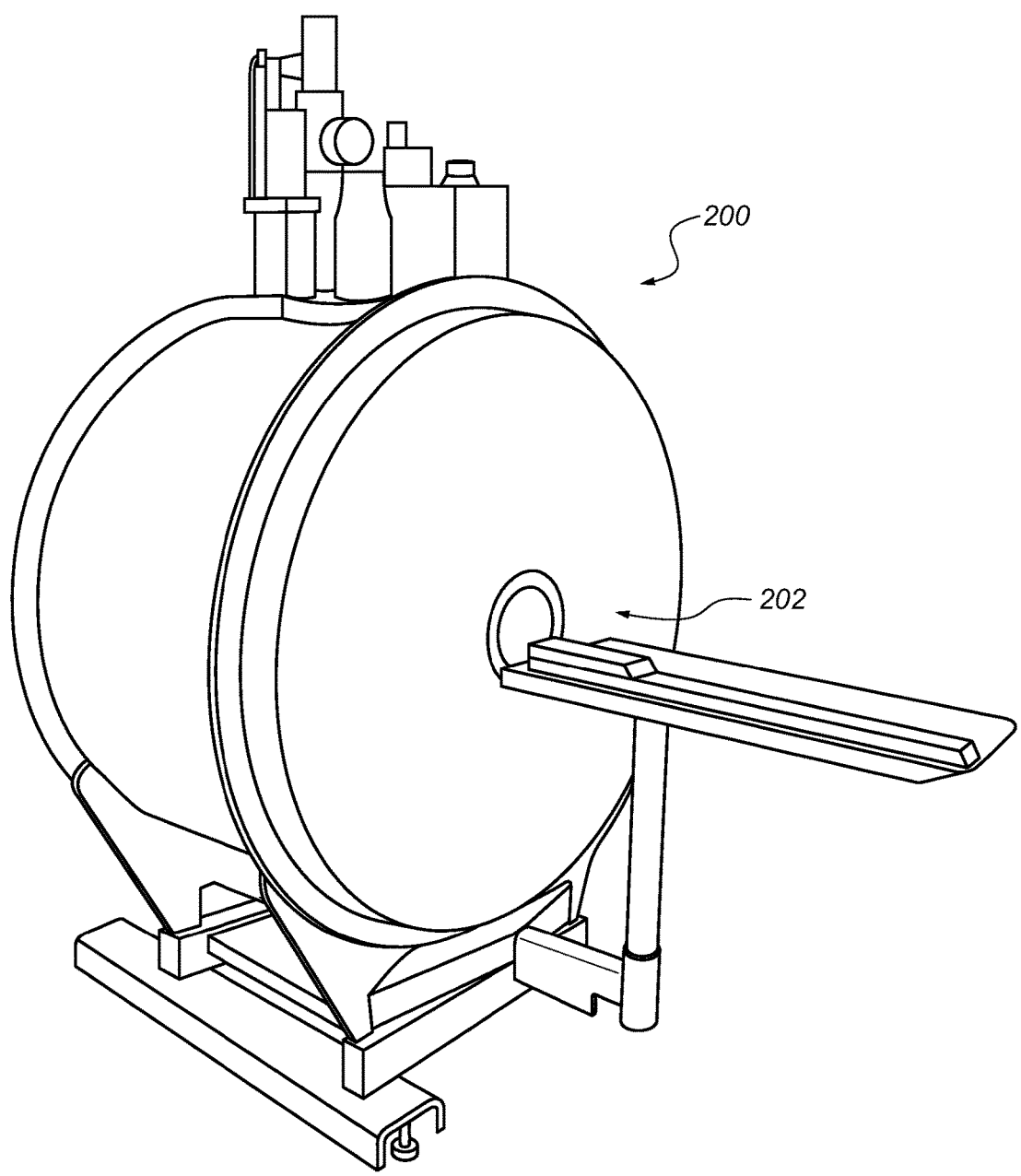
FIG. 4 is a perspective view of a Bruker 9.4 Tesla MRI device.

Turning to FIG. 4, the chamber 12 is now transported to an imaging device such as a Bruker MRI device 200. The Bruker MRI device 200 can, for example, have field strengths of 4.7, 7, 9.4 or 11.7 Tesla, and bore sizes that range from 16 to 40 cm. The imaging device can be a device that does medical imaging, medical scanning, X-ray radiography, medical ultrasonography or ultrasound, endoscopy, elastography, tactile imaging, thermography, medical photography, clinical imaging, clinical scanning, diagnostic imaging, radiological scanning, radiological imaging, and nuclear medicine functional imaging (e.g. positron emission tomography) or computed tomography. The MRI device 200 has a secondary cylinder (not shown) that is inserted into a bore 202 in the MRI device 200. The secondary cylinder includes a secondary coil and, in this example, a 35 mm bore which receives the chamber 12. The secondary coil is used to increase the resolution of the image by placing the coil much closer to the specimen in the chamber 12. After the chamber 12 is inserted into the secondary cylinder that resides in the bore 202, images of the specimen within the chamber 12 can be recorded. It is preferable that the conditioning frame 100 (FIG. 3) and the imaging device are located relatively close to each other.

Figure 5:
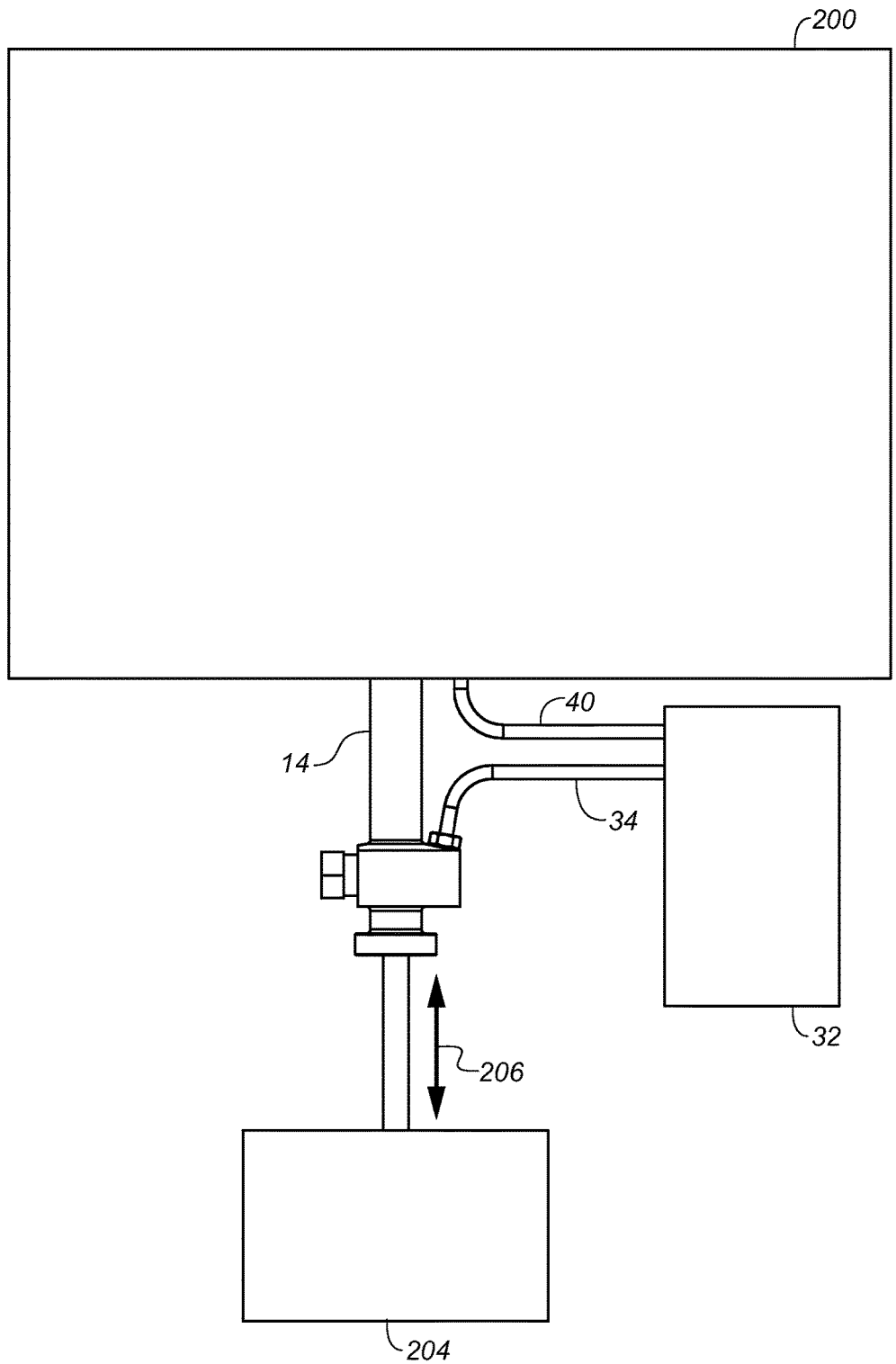
FIG. 5 is a schematic view of a conditioning and imaging system.

Referring to FIG. 5, a chamber 12 (not visible) has been inserted into the MRI device 200. The pump unit 32 is still connected to the fixture 14 via the conduit 34 and to the fixture 16 (not visible) via the conduit 40. As such, fluid flow through the chamber 12 can be maintained while the chamber is in the MRI device 200 and images of the specimen are being recorded. A conditioning system 204 is connected to the fixture 14 and can move the fixture back and forth in the direction of a double-headed arrow 206 to mechanically stimulate a specimen within the chamber 12 while the chamber is in the MRI device 200.

A number of implementations have been described. Nevertheless, it will be understood that additional modifications may be made without departing from the scope of the inventive concepts described herein, and, accordingly, other embodiments are within the scope of the following claims.

What is claimed is:

1. A conditioning system, comprising:
   a sample chamber capable of receiving a specimen, the sample chamber being sized and shaped so that it can be inserted into an MRI imaging device which can record images of the specimen;
   first and second specimen-holding fixtures positioned within the sample chamber and configured to rotate or displace along an axis to apply mechanical stimulation to the specimen held by the fixtures while the sample chamber is in the MRI imaging device, the first and second specimen-holding fixtures being formed of a material which does not interfere with the MRI imaging device; and
   at least one port capable of providing a fluid to the sample chamber.

2. The conditioning system of claim 1, wherein the sample chamber is in the shape of a cylinder.

3. The conditioning system of claim 2, wherein an outside diameter of the cylindrical chamber is sized so that the chamber can be received into a bore in the imaging device.

4. The conditioning system of claim 1, wherein the conditioning system includes one or more of plastic, thermoplastic, polyether ether ketone, polyvinylidene fluoride, polypropylene, silicone and polycarbonate.

5. The conditioning system of claim 1, wherein the first and second specimen-holding fixtures include polyether ether ketone.

6. The conditioning system of claim 1, in which the sample chamber includes at least one transparent window that includes one or more of polyvinylidene fluoride and polycarbonate.

7. The conditioning system of claim 1, wherein fluid flow through the chamber can be maintained while the chamber is in the imaging device.

8. The conditioning system of claim 1, wherein the conditioning system includes one or more materials (i)

having a dielectric strength of at least 7800 volts/mm, and (ii) which allow artifact free images of the specimen to be recorded.

9. The conditioning system of claim 1, wherein the conditioning system includes one or more materials (i) having a dielectric constant of between 2.2 to 8.4, and (ii) which allow artifact free images of the specimen to be recorded.

10. A conditioning system, comprising:
  a sample chamber capable of receiving a specimen, the sample chamber being sized and shaped so that it can be inserted into an MRI imaging device;
  first and second specimen-holding fixtures positioned within the sample chamber and configured to rotate or displace along an axis to apply mechanical stimulation to the specimen held by the fixtures while the sample chamber is in the MRI imaging device, the first and second specimen-holding fixtures being formed of a material which does not interfere with the MRI imaging device; and
  at least one port capable of providing a fluid to one or more of the sample and the sample chamber, the conditioning system being made of materials which allow the specimen contained in the sample chamber to be imaged by the imaging device into which the sample chamber has been inserted.

11. The conditioning system of claim 10, wherein the sample chamber is in the shape of a cylinder.

12. The conditioning system of claim 11, wherein an outside diameter of the cylindrical chamber is sized so that the chamber can be received into a bore in the imaging device.

13. The conditioning system of claim 10, wherein the conditioning system includes one or more of plastic, thermoplastic, polyether ether ketone, polyvinylidene fluoride, polypropylene, silicone and polycarbonate.

14. The conditioning system of claim 10, wherein the first and second specimen-holding fixtures include polyether ether ketone.

15. The conditioning system of claim 10, in which the sample chamber includes at least one transparent window that includes one or more of polyvinylidene fluoride and polycarbonate.

16. The conditioning system of claim 10, wherein fluid flow through the chamber can be maintained while the chamber is in the imaging device.

17. The conditioning system of claim 10, wherein the conditioning system includes one or more materials (i) having a dielectric strength of at least 7800 volts/mm, and (ii) which allow artifact free images of the specimen to be recorded.

18. The conditioning system of claim 10, wherein the conditioning system includes one or more materials (i) having a dielectric constant of between 2.2 to 8.4, and (ii) which allow artifact free images of the specimen to be recorded.

19. A method of conditioning and imaging a specimen, comprising:
  providing a sample chamber capable of receiving the specimen;
  placing the specimen into the chamber such that the specimen is located between first and a second specimen-holding fixtures positioned within the sample chamber;
  adjusting the fixtures so that the fixtures hold the specimen;
  applying mechanical stimulation to the specimen held by the fixtures by rotating or displacing at least one of the fixtures along an axis;
  inserting the chamber into an MRI imaging device;
  mechanically stimulating the specimen using at least one of the fixtures while the chamber is in the MRI imaging device, the first and second specimen-holding fixtures being formed of a material which does not interfere with the MRI imaging device; and
  recording an image of the specimen.

20. The method of claim 19, wherein the chamber is in the shape of a cylinder.

21. The method of claim 20, wherein an outside diameter of the cylindrical chamber is sized so that the chamber can be received into a bore in the imaging device.

22. The method of claim 19, wherein the chamber includes polypropylene.

23. The method of claim 19, wherein the first and second specimen-holding fixtures include polyether ether ketone.

24. The method of claim 19, in which the sample chamber includes at least one transparent window that includes one or more of polyvinylidene fluoride and polycarbonate.

25. The method of claim 19, further including providing at least one port in the chamber that is capable of providing a fluid to the sample chamber.

26. The method of claim 19, further including maintaining fluid flow through the chamber while the chamber is in the imaging device.

* * * * *